United States Patent
Saadeh et al.

(10) Patent No.: US 11,338,018 B2
(45) Date of Patent: May 24, 2022

(54) ADRENOCORTICOTROPIC HORMONE-BASED PHARMACEUTICAL FORMULATIONS AND METHODS FOR FABRICATING AND USING THEREOF

(71) Applicant: Harrow IP, LLC, Nashville, TN (US)

(72) Inventors: Dennis Elias Saadeh, Irvine, CA (US); Mark L. Baum, San Diego, CA (US)

(73) Assignee: Harrow IP, LLC, Nashville, TN (US)

( * ) Notice: Subject to any disclaimer, the term of this patent is extended or adjusted under 35 U.S.C. 154(b) by 0 days.

(21) Appl. No.: 16/250,711

(22) Filed: Jan. 17, 2019

(65) Prior Publication Data

US 2019/0134163 A1  May 9, 2019

Related U.S. Application Data

(63) Continuation-in-part of application No. 15/621,653, filed on Jun. 13, 2017, now abandoned.

(60) Provisional application No. 62/436,082, filed on Dec. 19, 2016.

(51) Int. Cl.
*A61K 38/35* (2006.01)
*A61P 19/02* (2006.01)
*A61P 37/06* (2006.01)

(52) U.S. Cl.
CPC .............. *A61K 38/35* (2013.01); *A61P 19/02* (2018.01); *A61P 37/06* (2018.01)

(58) Field of Classification Search
None
See application file for complete search history.

(56) References Cited

U.S. PATENT DOCUMENTS

| | | | | |
|---|---|---|---|---|
| 5,272,135 A | * | 12/1993 | Takruri | A61K 9/0014 514/15.2 |
| 10,232,018 B2 | * | 3/2019 | Knight | A61K 38/22 |
| 2003/0077297 A1 | * | 4/2003 | Chen | A61K 9/1617 424/400 |
| 2003/0166570 A1 | | 9/2003 | Thody et al. | |
| 2003/0180352 A1 | | 9/2003 | Patel et al. | |
| 2003/0185763 A1 | * | 10/2003 | Haslwanter | A61K 9/0043 424/45 |
| 2006/0128620 A1 | | 6/2006 | Brennan et al. | |
| 2009/0060868 A1 | | 3/2009 | Brody et al. | |
| 2009/0175821 A1 | | 7/2009 | Bridon et al. | |
| 2014/0322226 A1 | | 10/2014 | Knight et al. | |
| 2016/0207957 A1 | | 7/2016 | Barlos et al. | |
| 2018/0169191 A1 | | 6/2018 | Saadeh et al. | |

FOREIGN PATENT DOCUMENTS

| | | | |
|---|---|---|---|
| WO | WO2003-020299 | * | 1/2003 |
| WO | 2003/020299 A1 | | 3/2003 |
| WO | 2018/118115 A1 | | 6/2018 |

OTHER PUBLICATIONS

Sigma-Aldrich (<https://www.sigmaaldrich.com/content/dam/sigma-aldrich/docs/Sigma-Aldrich/Product_Information_Sheet/m0262pis.pdf> Feb. 28, 2014).*
Dumortier et al. (Pharmaceutical Research, Dec. 2006, vol. 23 (Issue 12), p. 2709-2728).*
Chonkar et al. (Smart Polymers in Nasal Drug Delivery; Indian J Pharm Sci. Jul. 2015 77(4); 367-375).*
Pharmaceutical Technology: Mannitol (<https://www.pharmaceutical-technology.com/products/mannitol/>Jul. 7, 2014).*
Cosyntropin Injection (NDA 22-028, <https://www.accessdata.fda.gov/drugsatfda_docs/label/2008/022028lbl.pdf>epub Sep. 21, 2006).*
Li et al. (Corticotropin (ACTH), p. 11—2012.*
SidleyChem (Application of CMC in Pharmaceutical Industry; Jul. 2013).*
Marques-Marinho et al. ("Cellulose and It's Derivatives Use in the Pharmaceutical Compounding Practice"; Chapter 8, Intech; 2013).*
Corticotrophin and its Synthetic analogues (British Medical Journal, vol. 2 No. 5660 Jun. 28, 1969, pp. 809-811).*
Crawford et al. (IV Fluids, What nurses need to know; Fluid and Electrolyte series, May, Nursing 2011, pp. 30-38).*
Barnes et al. "Intravenous Methylprednisolone for Multiple Sclerosis in Relapse," Journal of Neurology, Neurosurgery & Psychiatry, Feb. 1, 1985, 48:157-159.
PCT/US2017/037240 International Search Report and Written Opinion dated Sep. 11, 2017.
International Search Report and Written Opinion for PCT/US2020/013543 dated Apr. 21, 2020.
Hughes et al. "Chapter 29: Drug Doses, Corticotropin," The Harriet Lane Handbook Twenty-First Edition, May 2, 2017, 841.
Non-final office action for related U.S. Appl. No. 16/774,415, dated Sep. 27, 2021, 10 pages.
Final Office Action in related U.S. Appl. No. 16/250,711 dated Dec. 17, 2021, 19 pages.
Crawford, et al., "I.V. fluids, What nurses need to know" Fluid and Electrolyte Series, Nursing 2011, 2011, 30-38.
"Today's Drugs: Corticotrophin and Its Synthetic Analogues" The British Medical Journal, 1969, 2(5660): 809-811.

* cited by examiner

*Primary Examiner* — Julie Ha
*Assistant Examiner* — Tara L Martinez

(57) ABSTRACT

Pharmaceutical compositions for treating, mitigating or preventing autoimmune diseases and associated conditions are described herein. Methods for fabricating the compositions and using them are also described.

4 Claims, 2 Drawing Sheets
Specification includes a Sequence Listing.

SEQUENCE LISTING

<160> NUMBER OF SEQ ID NOS: 5

<210> SEQ ID NO 1
<211> LENGTH: 39
<212> TYPE: PRT
<213> ORGANISM: Artificial Sequence
<220> FEATURE:
<223> OTHER INFORMATION: Sythetic construct

<400> SEQUENCE: 1

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Leu Ala
            20                  25                  30

Glu Ala Phe Pro Leu Glu Phe
        35

<210> SEQ ID NO 2
<211> LENGTH: 24
<212> TYPE: PRT
<213> ORGANISM: Artificial Sequence
<220> FEATURE:
<223> OTHER INFORMATION: Synthetic construct

<400> SEQUENCE: 2

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 3
<211> LENGTH: 16
<212> TYPE: PRT
<213> ORGANISM: Artificial Sequence
<220> FEATURE:
<223> OTHER INFORMATION: Synthetic construct

<400> SEQUENCE: 3

Ser Tyr Ser Met Glu His Phe Arg Trp Gly Lys Pro Val Gly Lys Lys
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Synthetic construct

<400> SEQUENCE: 4

Ser Tyr Ser Met Glu His Phe Arg Trp Gly Lys Pro Val Gly Lys Lys
1               5                   10                  15

Arg

<210> SEQ ID NO 5
<211> LENGTH: 39
<212> TYPE: PRT
<213> ORGANISM: Artificial Sequence
<220> FEATURE:
<223> OTHER INFORMATION: Synthetic construct

<400> SEQUENCE: 5

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala

```
                20                  25                  30
Glu Ala Phe Pro Leu Glu Phe
        35
```

ADRENOCORTICOTROPIC HORMONE-BASED PHARMACEUTICAL FORMULATIONS AND METHODS FOR FABRICATING AND USING THEREOF

CROSS-REFERENCE TO RELATED APPLICATION(S)

This application is a continuation-in-part of U.S. Ser. No. 15/621,653, filed Jun. 13, 2017, currently pending, which claims priority under 35 U.S.C. § 119(e) to U.S. Provisional Application No. 62/436,082, filed on Dec. 19, 2016, the entire content of each of which is hereby incorporated by reference.

SEQUENCE LISTING

The instant application contains a Sequence Listing which has been submitted electronically in ASCII format and is hereby incorporated by reference in its entirety. The ASCII copy, created on Jan. 17, 2019, is named 20480-101795_SL.txt and is 3 KB in size.

FIELD OF THE INVENTION

The present invention relates generally to the field of treating autoimmune diseases and associated conditions, and more specifically to corticotropin-based compositions, to methods of using the compositions to treat, mitigate or prevent such diseases, and to methods of preparing such compositions.

BACKGROUND

Autoimmune diseases are caused by an attack of self-tissues by the immune system in response to an unknown trigger. Rheumatoid arthritis is a progressive autoimmune disease, affecting approximately 2% of the adult population of developed countries (Utsinger, P. D., et al., 1985 Rheumatoid Arthritis, p. 140). This disease is characterized by persistent inflammatory synovitis that causes destruction of cartilage and bone erosion, leading to structural deformities in the peripheral joints. The symptoms associated with rheumatoid arthritis include joint swelling, joint tenderness, inflammation, morning stiffness, and pain, especially upon flexing. Subjects having advanced stages of arthritis suffer from structural damage, including joint destruction with bone erosion. In addition, patients can present other clinical symptoms of various organic lesions, including lesions of the skin, kidney, heart, lung, central nervous system, and eyes due to vasculitis related to the autoimmune process.

Treatment for autoimmune diseases generally focuses on reducing immune system activity. Typical current treatments of such diseases include the use various oral or injectable medications, such as animal-derived corticotropin. One commonly used composition utilizing corticotropin is known under the trade name ACTHAR®, available from Mallinckrodt Pharmaceuticals (St. Louis, Mo.), and under other trade names. While animal-derived corticotropin may have certain beneficial properties, the existing corticotropin-based treatments, however, are of limited effectiveness in many patients and raise the risk of contamination by infectious agents of a protein nature, which may lead to development of degenerative encephalopathy. In addition, products made with animal-derived corticotropin may not conform to the dietary guidelines of vegetarians, Jewish kosher practitioners, or halal practitioners.

Accordingly, there exists a need for improved methods and compositions for treatment, mitigation and/or prevention of autoimmune diseases, such as Rheumatic diseases or disorders, and associated conditions that incorporate alternatives to animal-derived products. This patent specification discloses such pharmaceutical compositions that would achieve positive patient outcomes while being free of drawbacks and deficiencies of existing formulations, and methods of fabricating and administering the same.

SUMMARY

According to one embodiment of the invention, a pharmaceutical composition is provided. The composition comprises, consists essentially of, or consists of corticotropin of a non-animal derivation, wherein the composition is free of gelatin and free of preservatives.

According to another embodiment of the invention, the corticotropin used in the composition described herein comprises a quantity of one or several chemically synthesized and/or recombinant polypeptide(s) having the amino acid sequence(s) described herein below.

According to other embodiments of the invention, there are provided methods for treating, preventing or alleviating an autoimmune disease/disorder, condition, syndrome, symptom, pathology, or malady using such corticotropin-based compositions, such as treating prevent or alleviating Rheumatic diseases or disorders.

DETAILED DESCRIPTION

A. Terms and Definitions

Figure 1:
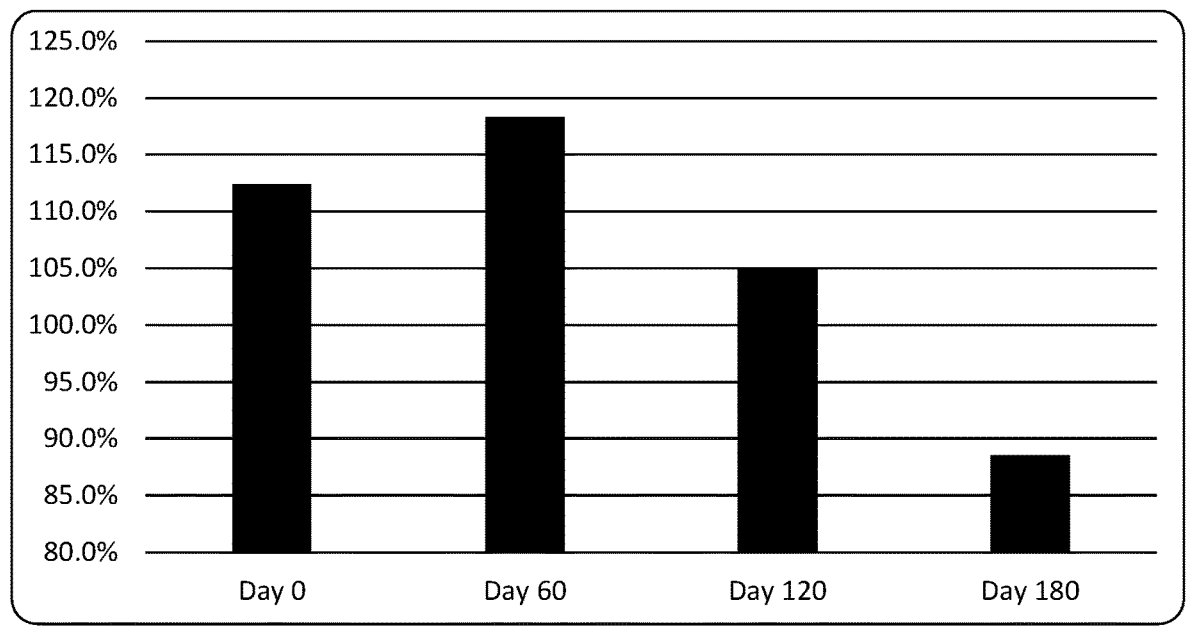
FIG. 1 is a graphical diagram showing potency of various exemplary compositions for up to 180 days.

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary only and are not restrictive of the invention as claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees, depending on the context. Whenever it appears herein, a numerical range such as "1 to 20" or "1-20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of a disease or pathology.

The terms "adrenocorticotropic hormone" (sometimes abbreviated hereinafter as "ACTH") and corticotropin are used hereinafter interchangeably and refer to a polypeptide tropic hormone produced by the anterior pituitary gland of a mammal. The structure and some basic properties of ACTH are discussed in more detail below. It is further provided that for the purposes of the present disclosure, a fully synthetic version of corticotropin and/or a recombinant version of corticotropin is considered to be ACTH/corticotropin of a non-animal derivation.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. Typically, polypeptides consist of more than 10 amino acid residues.

The term "recombinant" when used in reference to a polypeptide refers to a manipulated polypeptide that is generated in any of various known ways. For example, the formation of recombinant polypeptides may be carried out in specialized vehicles known as vectors, which are used to insert the recombinant polypeptide into a system that supports expression of the gene and translation of messenger RNA. Consequently, when DNA from a foreign source is linked to host sequences that can drive DNA replication and then introduced into a host organism, the foreign DNA is replicated along with the host DNA. Without being bound by theory, a recombinant polypeptide may be identical in every respect to the corresponding polypeptide of the same amino acid sequence that occurs naturally in living organisms.

The term "chemically synthesized" when used in reference to a polypeptide refers to synthetic polypeptides that are created by a condensation reaction of the carboxyl group of one amino acid to the amino group of another to form amide bonds linking each successive amino acid. Without being bound by theory, chemical peptide synthesis most commonly starts at the carboxyl end of the peptide (C-terminus), and proceeds toward the amino-terminus (N-terminus).

The term "autoimmune disease" refers to a pathological physiological state or condition in a human body that arises from abnormal acquired immune system's reactions of the body to substances and/or tissues that are normally present in the body.

The term "rheumatic disorder" refers to a variety of pathological physiological states or conditions in a human body that cause chronic pain affecting the joints and/or connective tissue. As used herein, this term is inclusive of both the disorders primarily caused by autoimmunity (e.g., rheumatoid arthritis, juvenile arthritis, gout, etc.) and the disorders of other origins (e.g., bursitis, osteoarthritis, spondylitis, etc.). Likewise, the term "rheumatic disease" encompasses a plethora of disorders that can affect any or many of the body's systems, but predominantly affect the joints and connective tissues. Many of these disorders tend to be chronic and often people have variable symptoms, experiencing periods of both exacerbation and remission in relation to both the type and severity of these symptoms. Rheumatic diseases are generally classified as inflammatory rheumatism, degenerative rheumatism, extra-articular rheumatism, or collagen diseases. Examples of the most common rheumatic diseases include, but are not limited to, osteoarthritis, rheumatoid arthritis, Fibromyalgia, lupus, gout, Juvenile idiopathic arthritis, Infectious arthritis, Psoriatic arthritis, Polymyositis, Bursitis, Ankylosing spondylitis, Reactive arthritis, Scleroderma, and Polymyalgia rheumatic.

The terms "infantile spasm" and "West syndrome" refer interchangeably to a specific type of seizure seen in an epilepsy syndrome of infancy and is characterized by developmental regression and by hypsarrhythmia (chaotic brain waves), which is a specific pattern on electroencephalography chart.

The term "Addison's disease" refers to an endocrine disorder in which the adrenal glands of the sufferer do not produce enough steroid hormones.

The term "Cushing's syndrome" refers to a condition characterized by increased secretion of adrenocorticotropic hormone resulting in multiple negative effects on the health of the patient, e.g., weight gain, hypertension, impaired immunological function, etc.

The term "Nelson's syndrome" refers to a disorder resulting from an adrenalectomy performed for Cushing's disease, wherein the patient develops macroadenomas that secrete adrenocorticotropic hormone resulting in various severe health problems.

The term "lupus" refers to a chronic inflammatory disease that occurs when a person's immune system attacks its own tissues and organs with severe and potentially deadly effects on many body systems, including blood cells, brain, heart, joints, skin, kidneys, and lungs.

The term "therapeutically effective amount" is defined as the amount of a compound or pharmaceutical composition that will elicit the biological or medical response of a tissue, system, animal or human, that is being sought by the researcher, medical doctor or other clinician.

The term "potency" is defined in accordance with the U.S. Pharmacopeia (USP) and refers to the quantity of an active pharmaceutical component in the composition. In accordance with the requirements of the USP, the potency that is required of the corticotropin compositions described below is not less than 80.0 percent and not more than 125.0 percent of the potency stated on the label in USP corticotropin units.

The term "USP unit" refers to a unit used to measure the mass of a vitamin or drug based on its expected biological effects. For each substance to which this unit applies, the U.S. Pharmacopeia has determined the biological effect associated with a dose of 1 USP unit. As such, quantities of the substance can be expressed in terms of this standard unit, which, in most cases, is equal to the international unit (IU). For example, 1 USP unit of synthetic porcine corticotropin equals approximately 10 micrograms, which equals 0.01 mg.

The term "pharmaceutically acceptable" when used to describe a carrier, whether diluent or excipient, is defined as being compatible with the other ingredients of the formulation and not deleterious to the recipient thereof.

The terms "administration of a composition" or "administering a composition" are defined to include the act of providing a compound or pharmaceutical composition of the invention to the subject in need of treatment.

B. Embodiments of the Invention

According to embodiments of the present invention, pharmaceutical compositions are provided for treating, mitigating or preventing various diseases, syndromes and maladies described below. The compositions include corticotropin of a non-animal derivation, completely synthetic in origin and are free of both gelatin and of any preservatives, e.g., are free of such a preservative as phenol. While some of ordinary skill in the art may consider cysteine or its related amino acids (e.g., methionine) as being among preservatives used in some applications, nevertheless, for the purposes of the instant disclosure, cysteine and related amino acids are defined as not being a preservative. The compositions of the present invention, therefore, may contain cysteine or related amino acids such as methionine, or, alternatively, may be cysteine-free and free of amino acids related to cysteine (such as methionine), as desired. Thus, the pharmaceutical compositions provided herein avoid the risk of contamination by infectious agents, which may lead to development of degenerative encephalopathy in a subject to which the composition is administered. In addition, being of non-animal derivation, the pharmaceutical compositions provided herein conform to the dietary guidelines of vegetarians, Jewish kosher practitioners, and halal practitioners.

Commercially available corticotropin (ACTH) is isolated from porcine pituitary extracts. This naturally occurring ACTH is a product of proteolytic cleavage (by the prohormone convertase) of the pro-hormone, proopiomelanocortin, which is secreted from corticotropes in the anterior lobe of the pituitary gland. Thus, natural ACTH is formed as a polypeptide tropic hormone having a 39-amino acid sequence and an average molecular weight of about 4, 540 Daltons.

As described above, the ACTH employed in the compositions described herein is a fully synthetic, and/or recombinant polypeptide having the same 39-amino acid sequence as the natural polypeptide. There are several known ways of synthesizing the synthetic and/or recombinant polypeptide and the resulting artificial polypeptide obtained by using any of these methods may be utilized. In addition to the full synthetic analog of natural ACTH, synthetic and/or recombinant polypeptides having the first 24, first 17, and first 16 amino acid residues of the 39-amino acid sequence may be prepared and used as described below.

Therefore, according to various embodiments of the invention, the corticotropin of a non-animal derivation used in the pharmaceutical compositions provided herein may include a recombinant polypeptide, a synthetically prepared polypeptide, or both a recombinant polypeptide and a synthetically prepared polypeptide. In various embodiments, the corticotropin used in the pharmaceutical compositions provided herein may be a mixture of one or more recombinant and/or synthetically prepared polypeptides of varying lengths (e.g., 39 amino acid residues, 24 amino acid residues, 17 amino acid residues, and 16 amino acid residues).

In various embodiments, the recombinant polypeptide in the composition is a polypeptide of non-animal derivation that includes the 39-amino acid sequence as set forth in SEQ ID NO: 1 (Synthetic Porcine Corticotropin), as shown below:

```
                                              (SEQ ID NO: 1)
SYSMEHFRWGKPVGKKRRPVKVYPNGAEDELAEAFPLEF.
```

If desired, any one or more of the 24-amino acid polypeptide as set forth in SEQ ID NO: 2, the 16-amino acid polypeptide as set forth in SEQ ID NO: 3, and the 17-amino acid polypeptide as set forth in SEQ ID NO: 4 may be present in the composition in addition to, or, if desired, instead of, the 39-amino acid polypeptide of SEQ ID NO: 1. SEQ ID NO: 2, SEQ ID NO: 3, and SEQ ID NO: 4 are as follows:

```
SYSMEHFRWGKPVGKKRRPVKVYP;    (SEQ ID NO: 2)

SYSMEHFRWGKPVGKK;            (SEQ ID NO: 3)

SYSMEHFRWGKPVGKKR.           (SEQ ID NO: 4)
```

Each of SEQ ID NO: 2, SEQ ID NO: 3, and SEQ ID NO: 4, correspond to the first 24, the first 16, and the first 17 amino acid residues, respectively, of the synthetically-prepared and/or recombinant polypeptide as set forth in SEQ ID NO: 1, and therefore are also of non-animal derivation.

In various embodiments, the recombinant polypeptide in the composition may be a polypeptide of non-animal derivation that includes the amino acid sequence as set forth in SEQ ID NO: 5 (Recombinant Human Corticotropin), as shown below:
 S

```
                                              (SEQ ID NO: 5)
SYSMEHFRWGKPVGKKRRPVKVYPNGAEDESAEAFPLEF.
```

It should be understood that SEQ ID NO: 5 may be used alone or in combination with one or more of SEQ ID NOs: 1-4 in the pharmaceutical compositions provided herein.

The quantity of the recombinant polypeptide or chemically synthesized polypeptide in the composition may be between about 40 USP units to about 120 USP units, such as between about 60 USP units to about 100 USP units, 70 USP units to about 90 USP units, for example, about 80 USP units.

As mentioned above, the pharmaceutical compositions described herein are preservative free, but may further optionally contain various inactive components. Some non-limiting examples of inactive components that may be so used include at least one inert water-soluble viscosity enhancing agent such as dextrose, mannitol, or carboxymethyl cellulose. Some non-limiting example(s) of additional water-soluble viscosity enhancing agent(s) that may be used instead of, or in addition to, dextrose, mannitol and/or carboxymethyl cellulose are cysteine, methyl cellulose, hydroxyethyl cellulose, hydroxypropyl cellulose, non-cross-linked or partially cross-linked polyacrylates.

The concentration of the water-soluble viscosity enhancing agent(s) described above, if used in the compositions, may be between about 0.5 mass % and 2.0 about mass % of the total mass of the composition, such as between about 1.0 mass % and about 1.5 mass %, for example, about 1.25 mass %.

According to further non-limiting embodiments, the preservative-free pharmaceutical compositions described herein may further optionally contain additional inactive component(s) that may be used in combination with, or instead of, the inactive component(s) described above. Non-limiting example(s) of such additional inactive component (s) include at least one non-ionic poly(oxyethlene-co-oxypropylene) block copolymer having the following general structure:

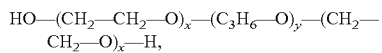

wherein in some further non-limiting embodiments, x is an integer that can have the value of at least 8 and y is an integer that can have the value of at least 38.

One non-limiting example of an even more specific non-ionic poly(oxyethlene-co-oxypropylene) block copolymer that can be used is the product known under the trade name Poloxamer 407® (P407) (poly(ethylene glycol)-block-poly(propylene glycol)-block-poly(ethylene glycol)) available from Sigma-Aldrich Corp. of St. Louis, Mo. (the trade name is owned by BASF Corp.), with the molecular weight of the polyoxypropylene portion of about 4,000 Daltons, about a 70% polyoxyethylene content, the overall molecular weight of between about 9,840 Daltons and about 14,600 Daltons. Another non-limiting example of a non-ionic poly(oxyethlene-co-oxypropylene) block copolymer that can be used is the product known under the trade name Poloxamer 188 (P188), which has an overall molecular weight of about 8400 Daltons. Each of which have the following chemical structure

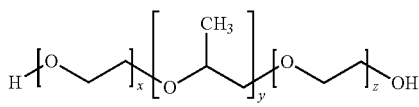

where x and z=80 and y=27 for P188; and where x and z=101 and y=56 for P407.

Other similar products of the POLOXAMER® family are useful for forming the thermoreversible gel of the compositions of the present invention are, for example, the products of the PLURONIC® family, KOLLIPHOR® family (the trade names are also owned by BASF) or SYNPERONICS® family (Croda International plc). Any polymer of POLOXAMER®, PLURONIC®, KOLLIPHOR® or SYNPERONICS® family that is used may contain any portion that is cross-linked.

The concentration of the non-ionic poly(oxyethlene-co-oxypropylene) block copolymer(s) described above, if used in the compositions, may be between about 0.1 mass and about 1.0 mass % of the total mass of the composition, for example, between about 0.1 mass % and about 2.0 mass %. In various embodiments the concentration of non-ionic poly(oxyethlene-co-oxypropylene) block copolymer(s) is about 0.3 mass %, about 0.5 mass %, about 0.7 mass %, or about 1.0 mass %.

Additional inactive component(s) include, but are not limited to, polyoxyethylene sorbitan monolaurates, polyoxyethylene sorbitan monopalmitates, polyoxyethylene sorbitan monostearates, and polyoxyethylene sorbitan monooleates.

According to further embodiments, methods for fabricating the above-described pharmaceutical articles are provided. A one-batch formulation method may be used, where the components of the pharmaceutical formulation are combined in single container; the components may be added to the container simultaneously or consecutively.

The resulting product may then be adapted for administration by a suitable route (e.g., by intramuscular or subcutaneous injection), and may then be prescribed and given to a patient for treating, mitigating or preventing autoimmune diseases, such as rheumatoid arthritis, as well as associated syndromes, symptoms, pathologies, maladies, or conditions.

It will be understood by those having ordinary skill in the art that the specific dose levels and frequency of administration for any particular patient may be varied and will depend upon a variety of factors including the activity of the specific compound employed, the metabolic stability and length of action of that compound, the age, body weight, general health, gender, diet, and the severity of the particular disease, syndrome, symptom, pathology, malady, or condition being treated.

It is also noteworthy that if an amino acid is used in compositions, the choice and concentration of the amino acid may be consequential. For example, in some experiments cysteine was used at a concentration of about 1 mg/ml. Such compositions lacked sufficient potency. On the other hand, using methionine instead of, or in addition to, cysteine, combined with increased concentration of the amino acid(s) up to about mg/ml can improved the potency substantially and to bring it to desirable level. Using mannitol has also proved to be beneficial for increasing the potency. Some comparative data regarding the potency of some compositions is provided below in the "Examples" portion of the application.

In additional embodiments, the above described pharmaceutical formulations may be incorporated within microparticles. The microparticles may be substantially spherical particles (shells) fabricated of a water-soluble biodegradable polymer defining a space therein, which space is to be filled with the pharmaceutical formulation. Thus, the microparticles represent the structures where the water-soluble biodegradable polymer envelops the formulation securely encapsulating the latter and not allowing the formulation to prematurely escape or to leak out.

The formulation-filled microparticles can be manufactured according to methods and techniques known to those having ordinary skill in the art. The size of microparticles may be typically less than about 100 μm in diameter, and the exemplary water soluble polymer to be used to manufacture the shells may be, without limitations, any of poly(lactic acid-co-glycolic acid), poly(lactic acid), poly(glycolic acid), poly(caprolactone), poly(hydroxybutyrate) and blends thereof. In one typical example, poly(lactic acid-co-glycolic acid) can be used to form the shells, with the 50:50 (mass) ratio between the units derived of lactic and glycolic acids. Other acceptable ratios between the lactic and glycolic acid portions may be 65:35, 75:25 and 85:15. Those having ordinary skill in the art and using poly(lactic acid-co-glycolic acid) may select a different ratio, if desired. The inherent viscosities (i.e., the ratio of the natural logarithm of the relative viscosity to the mass concentration of the polymer) of the polymer solutions used to form the shells may be between about 0.15 dL/g and about 1.20 dL/g, such as between about 0.15 dL/g and 0.25 dL/g, or of the following ranges: 0.26-0.54, 0.55-0.75, 0.62-0.65, 0.65-0.85, 0.76-0.94 and 0.95-1.20 dL/g.

When the above described microparticles have been fabricated, they can then be administered to a patient in need of the medication by conventional methods described herein, such as by injection.

In additional embodiments, pharmaceutical kits are provided. The kits include sealed containers approved for the storage of pharmaceutical compositions, and the above-described pharmaceutical composition. An instruction for the use of the composition and the information about the composition are to be included in the kit.

The following examples are provided to further elucidate the advantages and features of the present invention but are not intended to limit the scope of the invention. The examples are for the illustrative purposes only. USP pharmaceutical grade products were used in preparing the formulations described below.

Example 1. Preparing a Pharmaceutical Composition No. 1

A pharmaceutical composition can be prepared as described below. The following products can be used in the amounts and concentrations specified:
(a) about 8000 USP units of powdered chemically synthesized Porcine adrenocorticotropic hormone ACTH;
(b) about 0.3 g of powdered cysteine;
(c) about 5.0 g of powdered mannitol;
(d) about 50.0 mL of a 2.5% aqueous solution of sodium carboxymethyl cellulose;
(e) a quantity of a 10% aqueous solution of hydrochloric acid for adjusting pH; and
(f) about 100.0 mL of sterile water suitable for injections.

To prepare the composition, the stated quantities of cysteine and mannitol may be mixed with about 30% of water (about 30 mL) followed by adding ACTH to the solution which can then be filtered into a sterile 100 mL vial through a 0.22 micron Teflon filter. Finally, the stated amount of sodium carboxymethyl cellulose may be added to the vial followed by agitation to achieve dispersion. Alternatively, the dispersion may be achieved by using the method of "transferring from syringe to syringe" known to those having ordinary skill in the art.

The product so obtained can then be checked for the level of pH, and if this level is outside the range of about 4.5 to about 7.0, it can be adjusted by adding, dropwise, a quantity of hydrochloric acid that is necessary to achieve such an adjustment. The product can then be transferred into 1 mL sterile amber serum vials with about 0.2 mL overfill.

Example 2. Preparing a Pharmaceutical Composition No. 2

A pharmaceutical composition was prepared as described in Example 1 using the same components in the same quantities and employing the same compounding procedure, except that cysteine was replaced by about 0.298 g of powdered 0.3% methionine.

Example 3. Preparing a Pharmaceutical Composition No. 3

A pharmaceutical composition was prepared as described below. The following products were used in the amounts and concentrations specified:
(a) about 8000 USP units of powdered chemically synthesized Porcine adrenocorticotropic hormone ACTH;
(b) about 0.298 g of powdered methionine;
(c) about 5.0 g of powdered mannitol;
(d) about 0.3 g of POLOXAMER 188®;
(e) about 50.0 mL of a 2.5% aqueous solution of sodium carboxymethyl cellulose;
(f) a quantity of a 10% aqueous solution of hydrochloric acid for adjusting pH; and
(g) about 100.0 mL of sterile water suitable for injections.

To prepare the composition, the stated quantities of methionine and mannitol were mixed with about 30% of water (about 30 mL) followed by adding ACTH to the solution which was then filtered into a sterile 100 mL vial through a 0.22 micron Teflon filter. Finally, the stated amount of sodium carboxymethyl cellulose was added to the vial followed by agitation to achieve dispersion. Alternatively, the dispersion may be achieved by using the method of "transferring from syringe to syringe" known to those having ordinary skill in the art. The product can then be transferred into 1 mL sterile amber serum vials with about 0.2 mL overfill.

Figure 2:
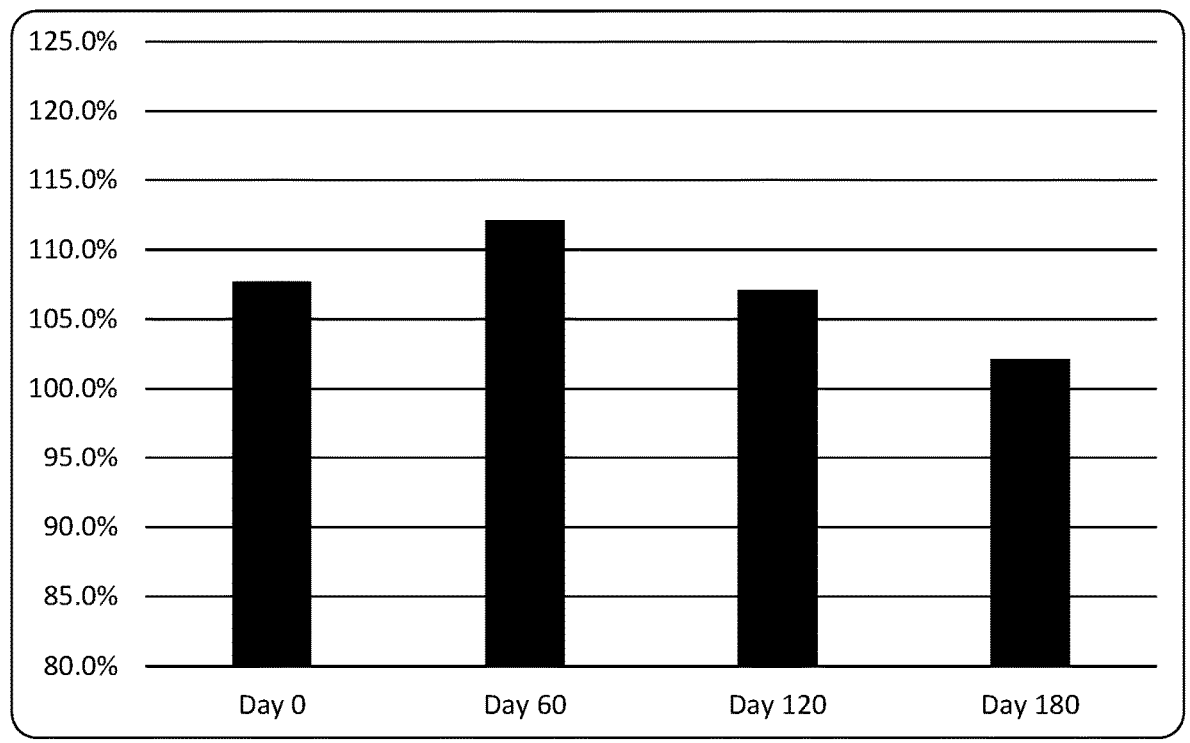
FIG. 2 is a graphical diagram showing potency of various exemplary compositions for up to 180 days.
Figure 3:
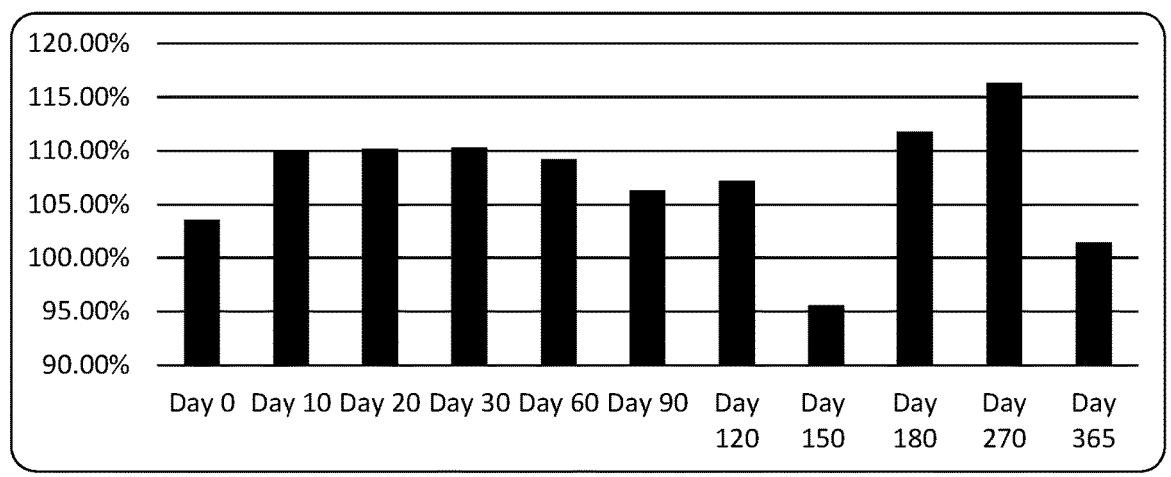
FIG. 3 is a graphical diagram showing potency of an exemplary composition for up to 365 days.
Figure 4:
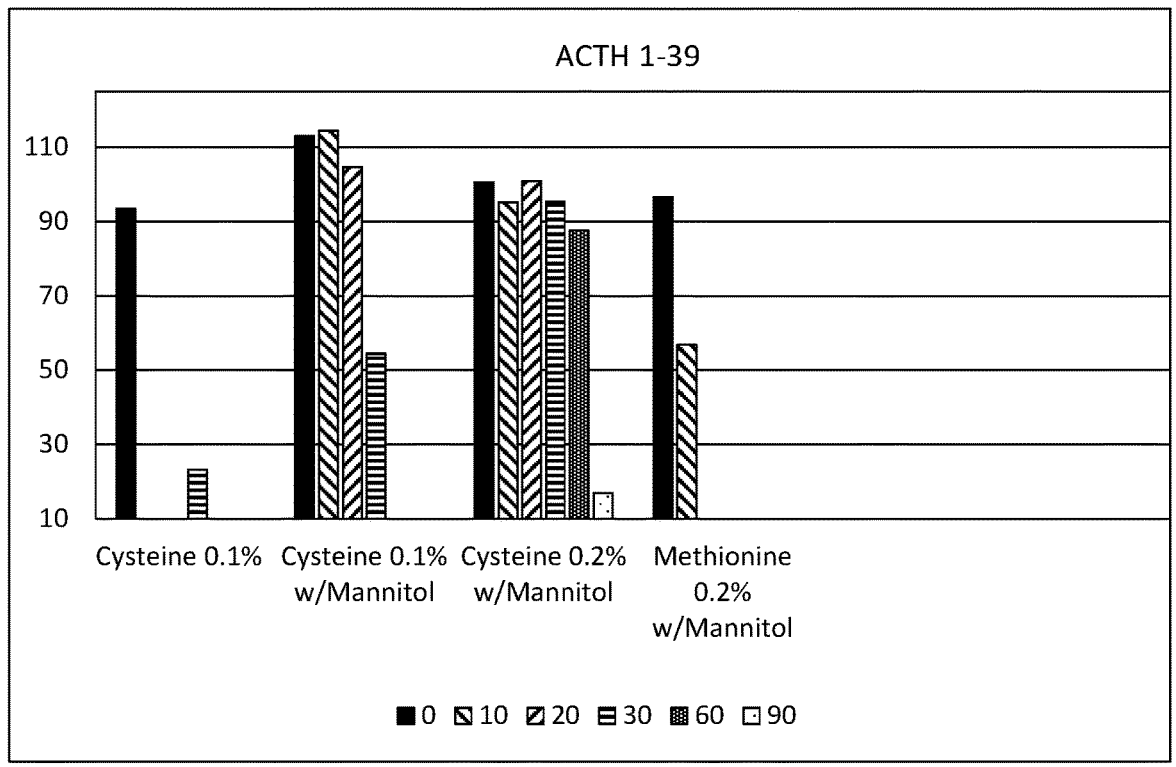
FIG. 4 is a graphical diagram showing potency of various exemplary compositions for up to 90 days.

Example 4. Comparative Potency Data to Assess Formulation Stability of Some Pharmaceutical Compositions Several compositions were prepared according to the methods illustrated in Examples 1-3. Table 1 provides a comparison of their respective potencies for showing shelf stability. The terms "recombinant porcine" and "recombinant human" refer to synthetic ACTH having the same amino acid sequence as the naturally occurring polypeptide derived from pigs and humans, respectively. As can be seen from the data presented in Table 1, using methionine provides corticotropin potency results that are considered unexpected based on the review of the corticotropin potency data shown by cysteine-containing compositions. Unexpectedly, it was observed that addition of L-Methionine in combination with Mannitol improved the shelf stability of Corticotropin Active Pharmaceutical Ingredient. FIGS. 1-4 show potencies of various exemplary compositions from Day 0 to Day 365.

TABLE 1

Select Compositions and Their Potencies

| ACTH | Amino acid | Mannitol | pH | Potency |
|---|---|---|---|---|
| Synthetic porcine | Cysteine, 1 mg/mL | None | 4.5-6.5 | Failed[1] after 30 days |
| Synthetic porcine | Cysteine, 2 mg/mL | Yes, 50 mg/mL | 4.0-6.0 | Failed after 10 days[2] |
| Synthetic porcine | Methionine, 2 mg/mL | Yes, 50 mg/mL | 4.0-6.0 | Failed after 10 days[2] |
| Recombinant human | Cysteine, 2 mg/mL | Yes, 50 mg/mL | 4.5-6.5 | Failed after 60 days[3] |
| Recombinant human | Methionine, 2 mg/mL | Yes, 50 mg/mL | 4.5-6.5 | Passed[4], stable after 180 days |
| Synthetic porcine | Cysteine, 2 mg/mL | Yes, 50 mg/mL | 4.5-6.6 | Failed after 30 days |
| Synthetic porcine | Methionine, 3 mg/mL | Yes, 50 mg/mL | 4.0-6.0 | Passed, stable after 365 days |
| Synthetic porcine | Methionine, 3 mg/mL + POLOXAMER 188®, 3 mg/mL | Yes, 50 mg/mL | 5.0-6.5 | Passed, stable after 360 days |

[1]"Failed" refers to the potency after the testing being outside of the USP Corticotropin Units 80-125% range required by the U.S. Pharmacopeia.
[2]Tested both at accelerated (room temperature) and refrigerated (real time) conditions; the failure applies to both conditions.
[3]Followed by even more substantial failure by day 90 (when only about 16.9% of the label amount remaining intact).
[4]"Passed" refers to the potency after the testing being within the 80-125% range required by the U.S. Pharmacopeia.

Although the invention has been described with reference to the above described embodiments, it will be understood that modifications and variations are encompassed within the spirit and scope of the invention. Accordingly, the invention is limited only by the following claims.

What is claimed is:

1. A pharmaceutical composition, consisting of:
(a) a therapeutically effective quantity of corticotropin, ACTH, of a non-animal derivation;
(b) a water-soluble viscosity enhancing agent selected from the group consisting of carboxymethyl cellulose, dextrose, methyl cellulose, hydroxyethyl cellulose, hydroxypropyl cellulose, non-cross-linked or partially cross-linked polyacrylates, and any combination thereof;
(c) an amino acid selected from the group consisting of cysteine, methionine, and any combination thereof; and
(d) water,
wherein the composition is free of gelatin and free of preservatives, with the further proviso that the pharmaceutical composition is adapted for administration by an injection.

2. A pharmaceutical composition, consisting of:
(a) a therapeutically effective quantity of corticotropin of a non-animal derivation;
(b) methionine;
(c) a water-soluble viscosity enhancing agent selected from the group consisting of carboxymethyl cellulose, dextrose, methyl cellulose, hydroxyethyl cellulose, hydroxypropyl cellulose, non-cross-linked or partially cross-linked polyacrylates, and any combination thereof;
(d) at least one inactive component selected from the group consisting of a non-ionic poly(oxyethlene-co-oxypropylene) block copolymer, a polyoxyethylene sorbitan monolaurate, a polyoxyethylene sorbitan monopalmitate, a polyoxyethylene sorbitan monostearate, and a polyoxyethylene sorbitan monooleate, wherein the at least one inactive component has a concentration of no more than 1% (w/v) of the composition;
(e) mannitol;
(f) a quantity of a pH adjusting agent selected from the group consisting of hydrochloric acid and sodium hydroxide; and
(g) water,
wherein the composition is free of gelatin and free of preservatives, with the further proviso that the pharmaceutical composition is adapted for administration by an injection.

3. The pharmaceutical composition of claim 2, wherein the corticotropin comprises one or more of a recombinant polypeptide and a chemically synthesized polypeptide.

4. The pharmaceutical composition of claim 3, wherein the recombinant polypeptide or the chemically synthesized polypeptide has the amino acid sequence selected from the group consisting of SEQ ID NO: 1, SEQ ID NO: 3, SEQ ID NO: 4, SEQ ID NO: 5, and any combination thereof.

* * * * *